United States Patent [19]
Kucar

[11] Patent Number: 5,700,146
[45] Date of Patent: Dec. 23, 1997

[54] DENTAL HYGIENE CLEANING TOOL

[76] Inventor: Smiljana Kucar, 222 Ocean Ave., Northport, N.Y. 11768

[21] Appl. No.: 568,535

[22] Filed: Dec. 7, 1995

[51] Int. Cl.[6] .................. A61C 1/10; A61C 1/12; A61C 17/02
[52] U.S. Cl. .................. 433/82; 601/162; 15/24; 132/322
[58] Field of Search .................. 601/162, 141; 132/321, 322; 433/80, 82, 87, 118; 401/163, 169; 15/24, 22.2

[56] References Cited

U.S. PATENT DOCUMENTS

| | | | |
|---|---|---|---|
| 4,060,870 | 12/1977 | Cannarella | 15/24 |
| 4,236,889 | 12/1980 | Wright | 601/162 |
| 4,845,795 | 7/1989 | Crawford et al. | 15/22.1 |
| 4,880,832 | 11/1989 | Moret et al. | 433/118 |
| 5,123,841 | 6/1992 | Millner | 601/141 X |
| 5,197,460 | 3/1993 | Ito et al. | 601/162 |
| 5,208,933 | 5/1993 | Lustig et al. | 15/24 X |
| 5,286,192 | 2/1994 | Dixon | 601/162 X |

*Primary Examiner*—Nicholas D. Lucchesi
*Attorney, Agent, or Firm*—Michael I. Kroll

[57] ABSTRACT

A dental hygiene cleaning tool (12) comprising an elongated generally cylindrical housing (14) to be grasped by a hand (16) of a person. A brush bit (18) is provided. A structure (20) is for coupling the brush bit (18) to a first end of the housing (14). A component (22) within the housing (14) is for rotating the brush bit (18). An element (24) within the housing (14) is for reciprocating the brush bit (18) back and forth, so as to clean plaque build up on teeth (26) and gums (28) of a person (30), to remove bacteria which causes periodontal disease to the gums (28).

28 Claims, 7 Drawing Sheets

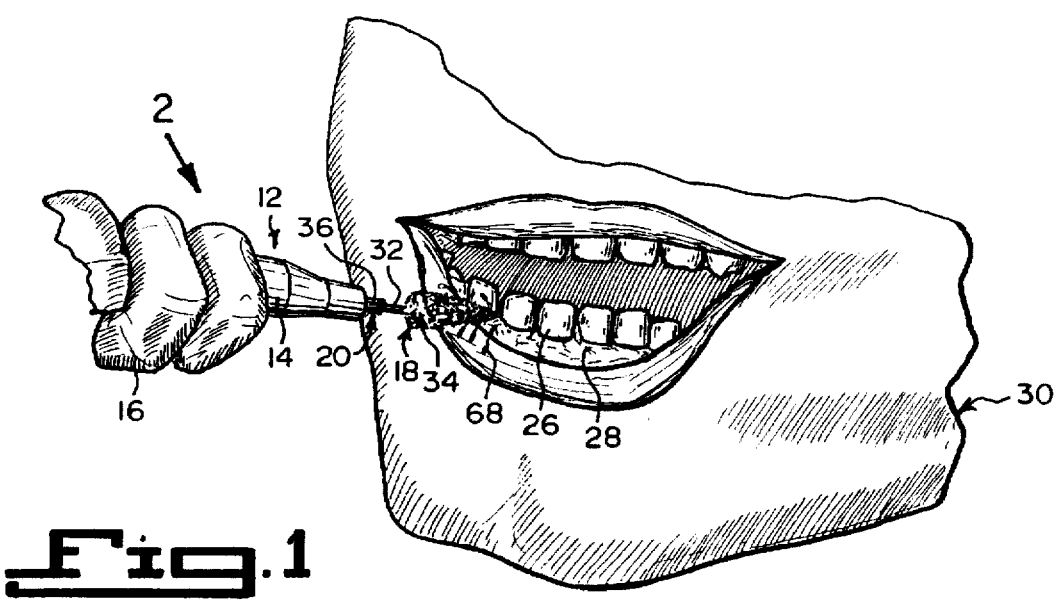
Fig.1
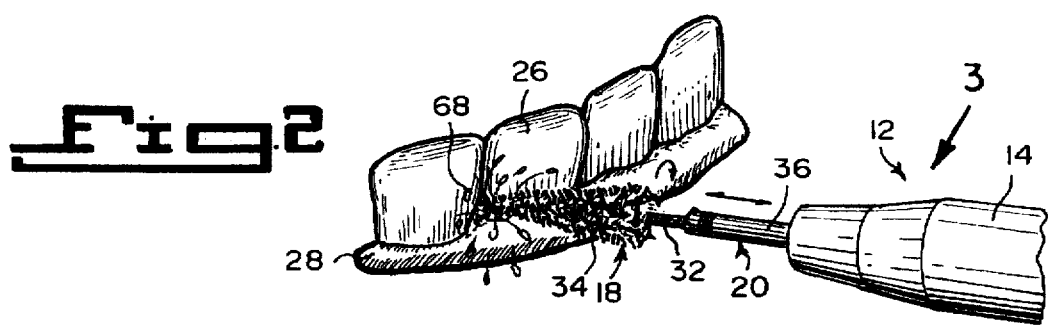
Fig.2
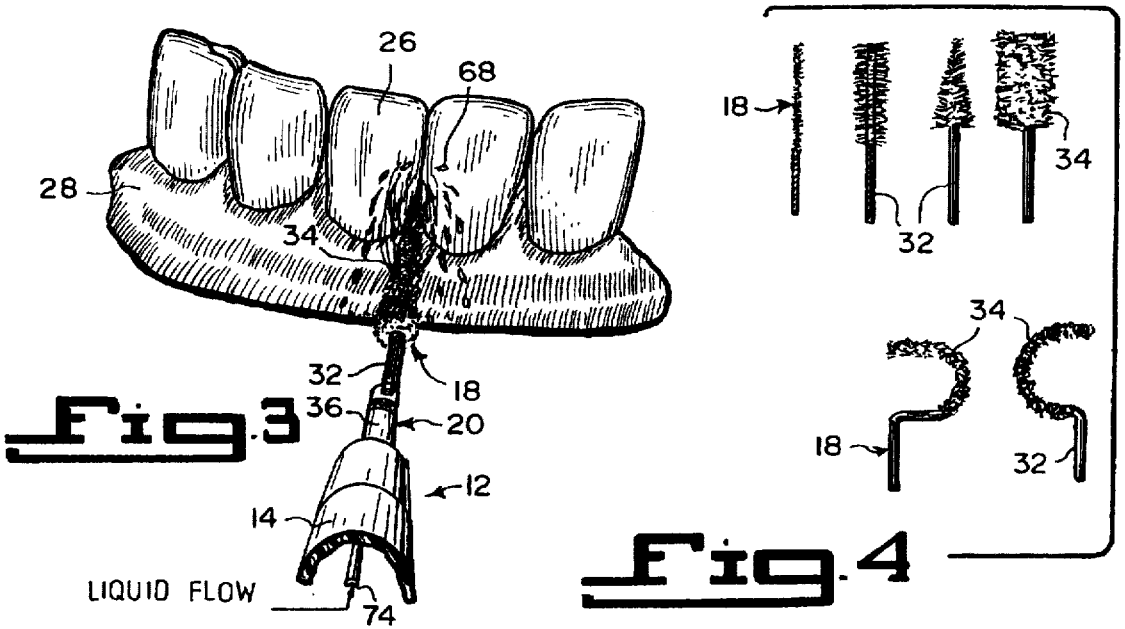
Fig.3
Fig.4
LIQUID FLOW

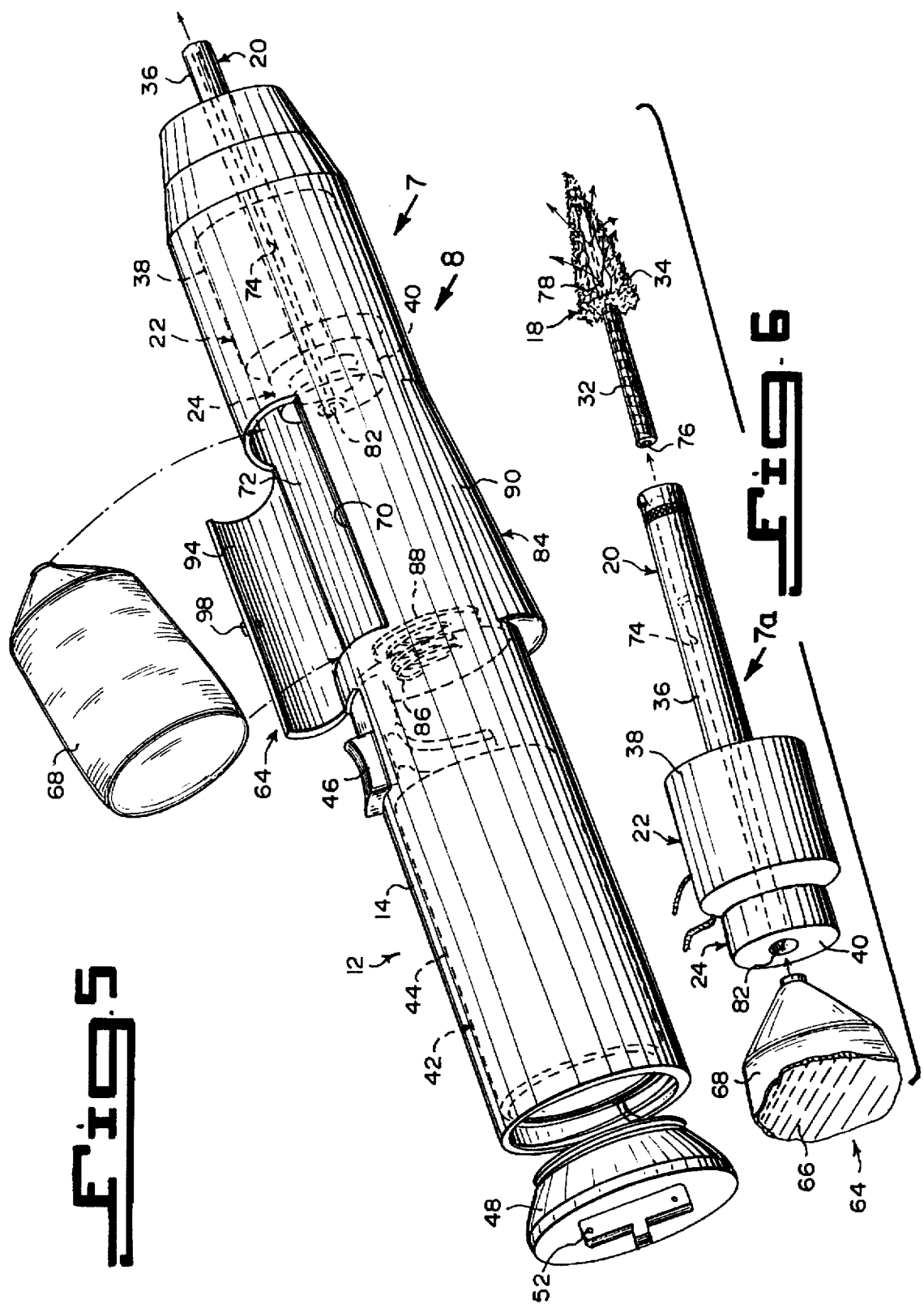

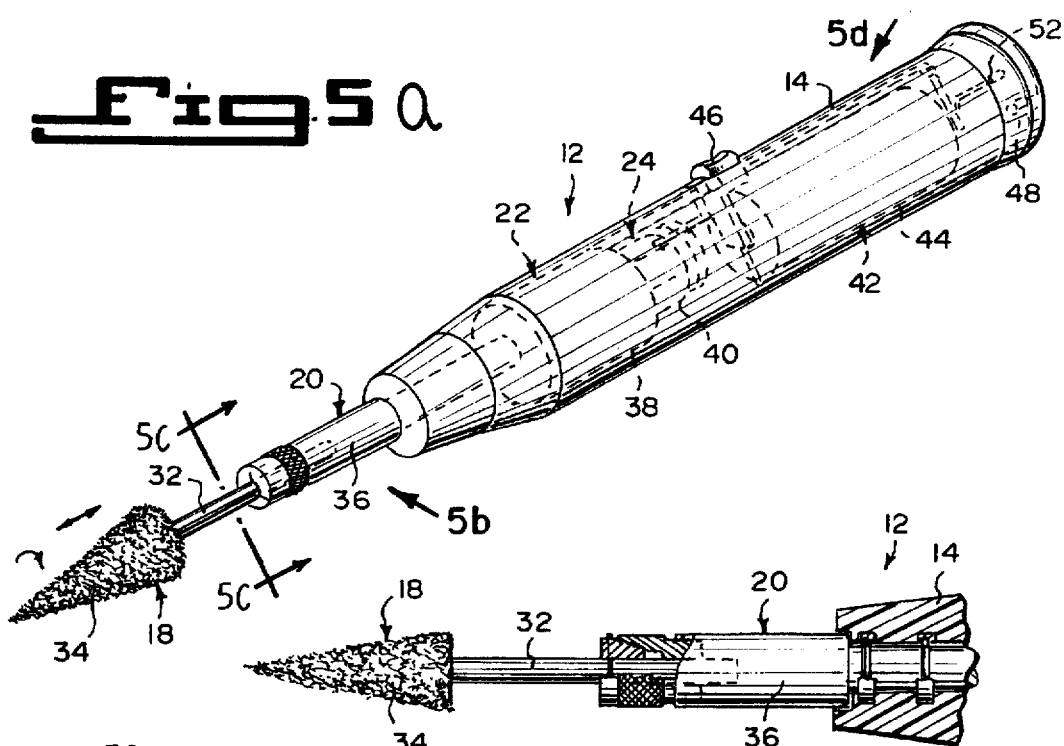
Fig.5a
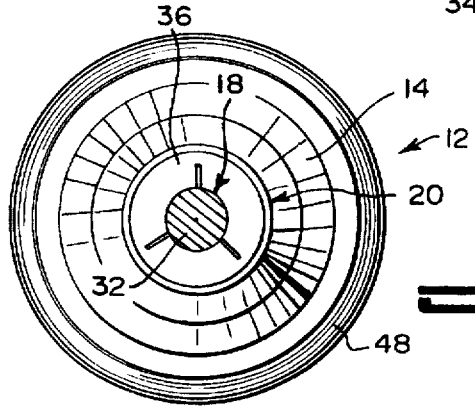
Fig.5b
Fig.5c
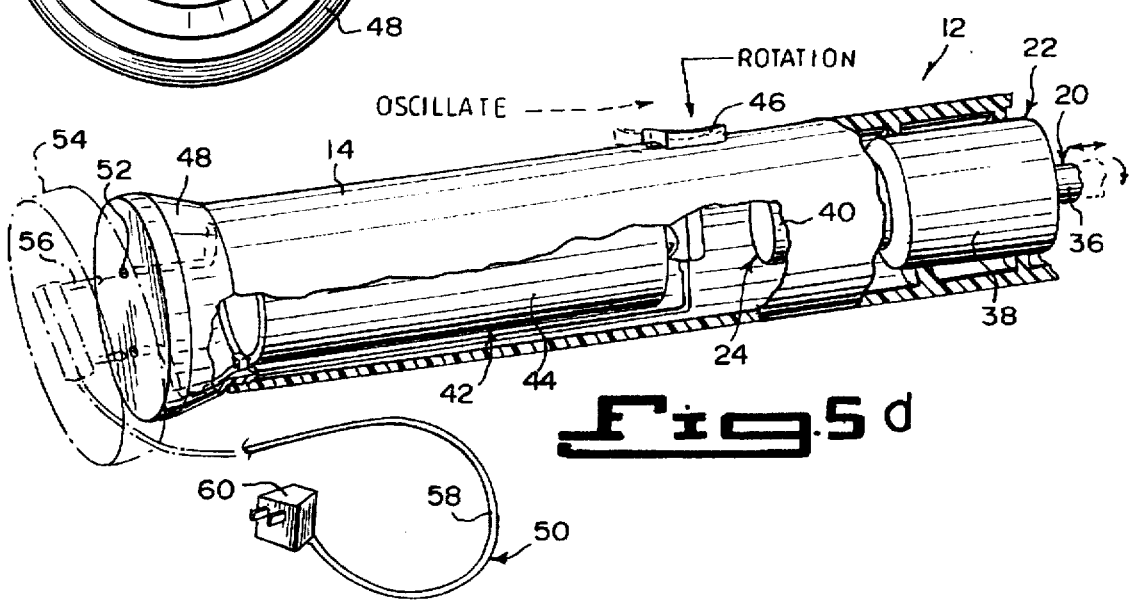
Fig.5d

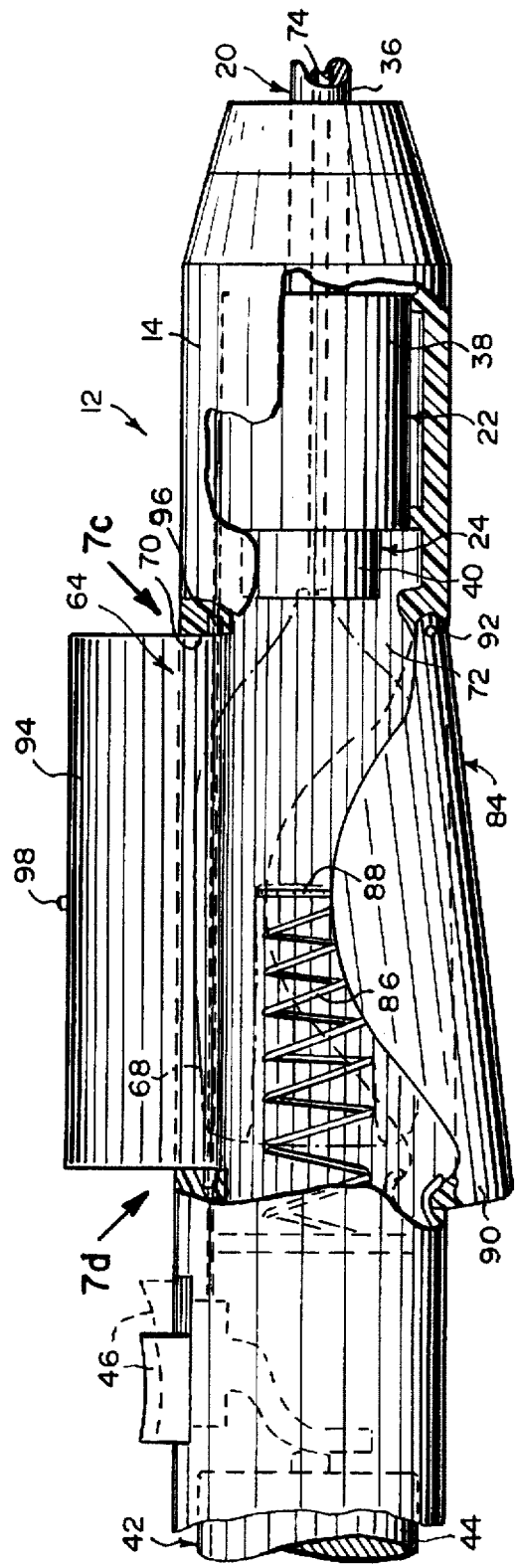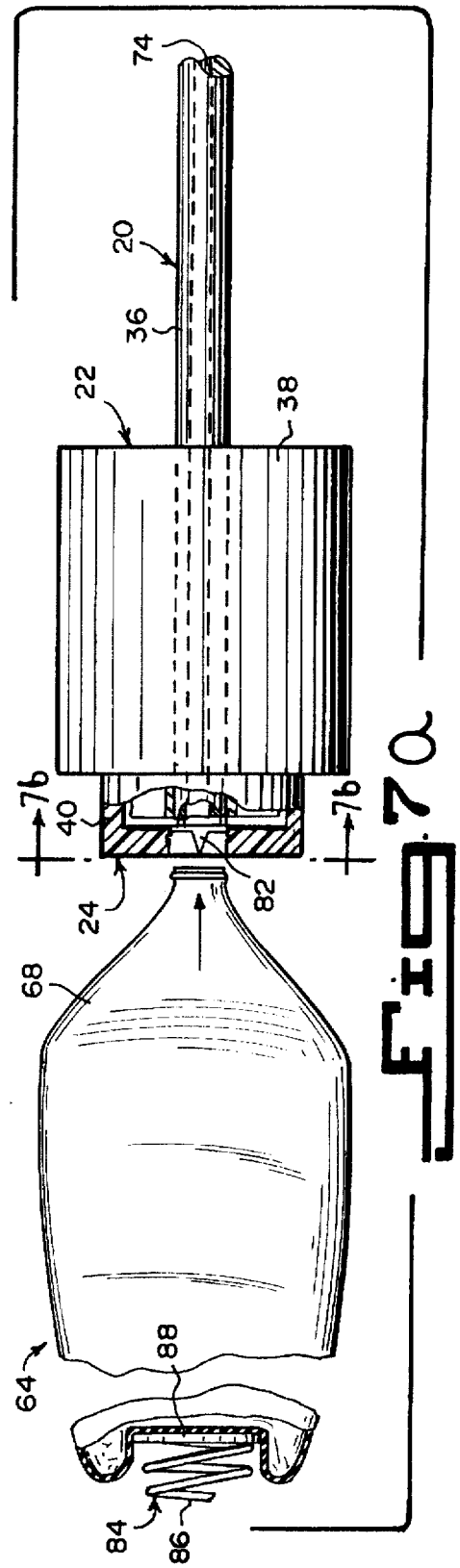

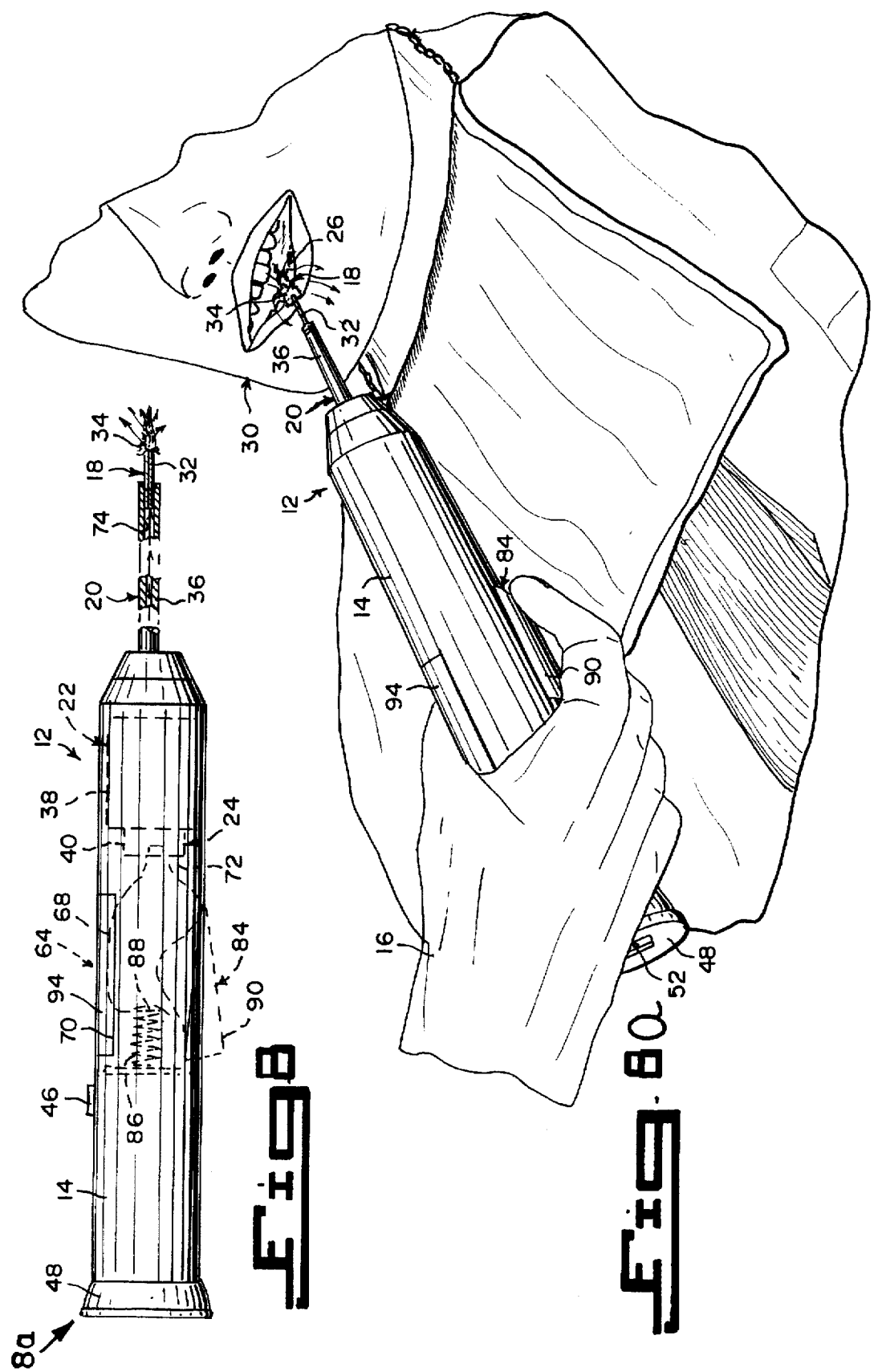

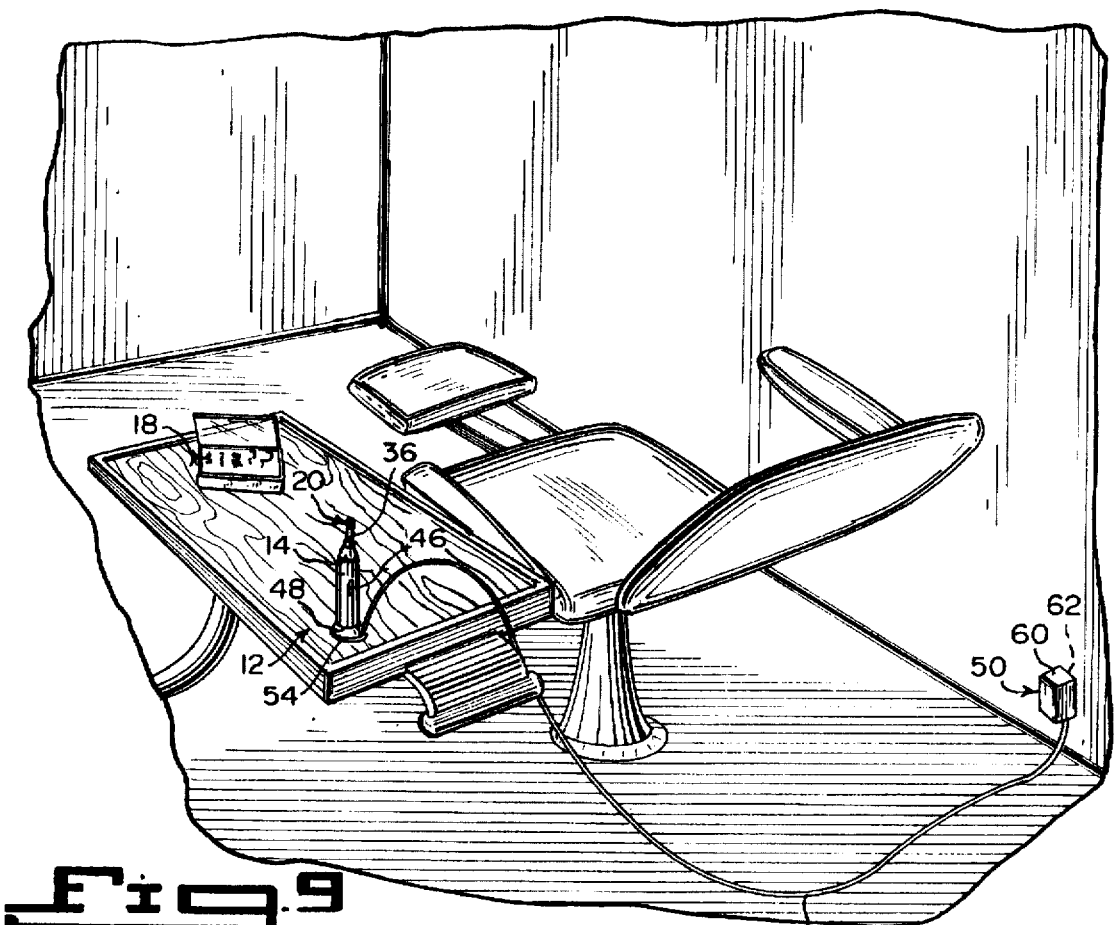
Fig. 9
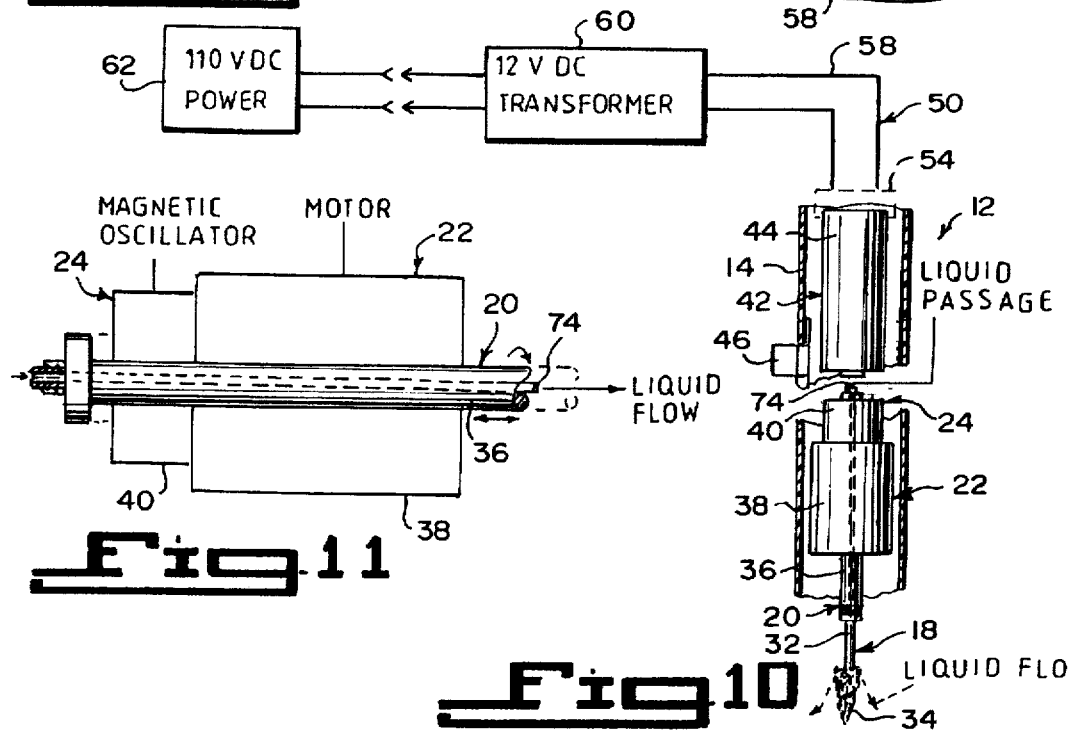
Fig. 11
Fig. 10

5,700,146

1

DENTAL HYGIENE CLEANING TOOL

BACKGROUND OF THE INVENTION

1. Field of the Invention

The instant invention relates generally to dental equipment and more specifically it relates to a dental hygiene cleaning tool.

2. Description of the Prior Art

Numerous dental equipment have been provided in prior art that are adapted to be utilized in taking care of the teeth and gums. While these units may be suitable for the particular purpose to which they address, they would not be as suitable for the purposes of the present invention as heretofore described.

SUMMARY OF THE INVENTION

A primary object of the present invention is to provide a dental hygiene cleaning tool that will overcome the shortcomings of the prior art devices.

Another object is to provide a dental hygiene cleaning tool that will clean the plaque build up on the teeth and gums, thereby removing the bacteria which causes periodontal disease to the gums.

An additional object is to provide a dental hygiene cleaning tool that can utilize a liquid antiseptic cartridge in conjunction with an oscillating and rotating brush head to help keel and remove the bacteria which causes the periodontal disease to the gums.

A further object is to provide a dental hygiene cleaning tool that is simple and easy to use.

A still further object is to provide a dental hygiene cleaning tool that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein;

FIG. 1 is a right side perspective view showing a first embodiment of the instant invention in use cleaning the teeth and gums in a mouth of a person.

FIG. 2 is a left side perspective view taken in the direction of arrow 2 in FIG. 1.

FIG. 3 is a top perspective view taken in the direction of arrow 3 in FIG. 2.

FIG. 4 is an elevational view showing various brush bits used in conjunction with the instant invention.

FIG. 5 is a partly exploded rear perspective view of the first embodiment.

FIG. 5a is a front perspective view of a second embodiment of the instant invention.

2

FIG. 5b is an elevational view with parts broken away and in section taken in the direction of arrow 5b in FIG. 5a.

FIG. 5c is a cross sectional view taken along line 5c—5c in FIG. 5a.

FIG. 5d is a rear perspective view with parts broken away and in section taken in the direction of arrow 5d in FIG. 5a, showing a battery charger partly in phantom ready to be plugged into the base.

FIG. 6 is an exploded perspective view of a portion of the first embodiment with the housing removed therefrom.

FIG. 7 is an elevational view with parts broken away and in section taken in the direction of arrow 7 in FIG. 5.

FIG. 7a is an exploded elevational view with parts broken away and in section taken in the direction of arrow 7a in FIG. 6.

Figure 7B:
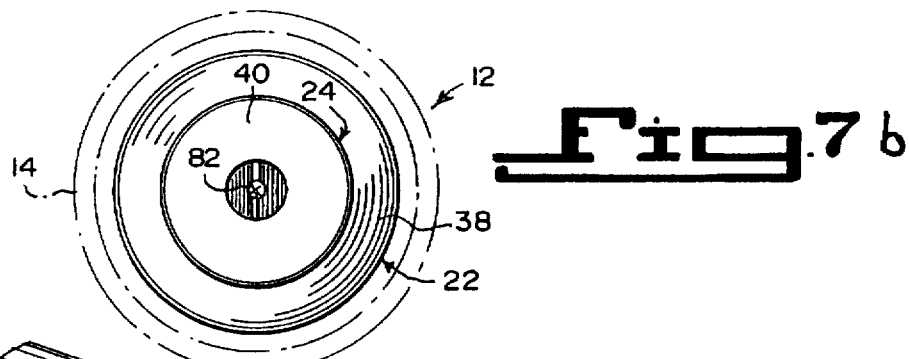

FIG. 7b is an end view taken along line 7b—7b in FIG. 7a with the housing shown in phantom.

Figure 7C:
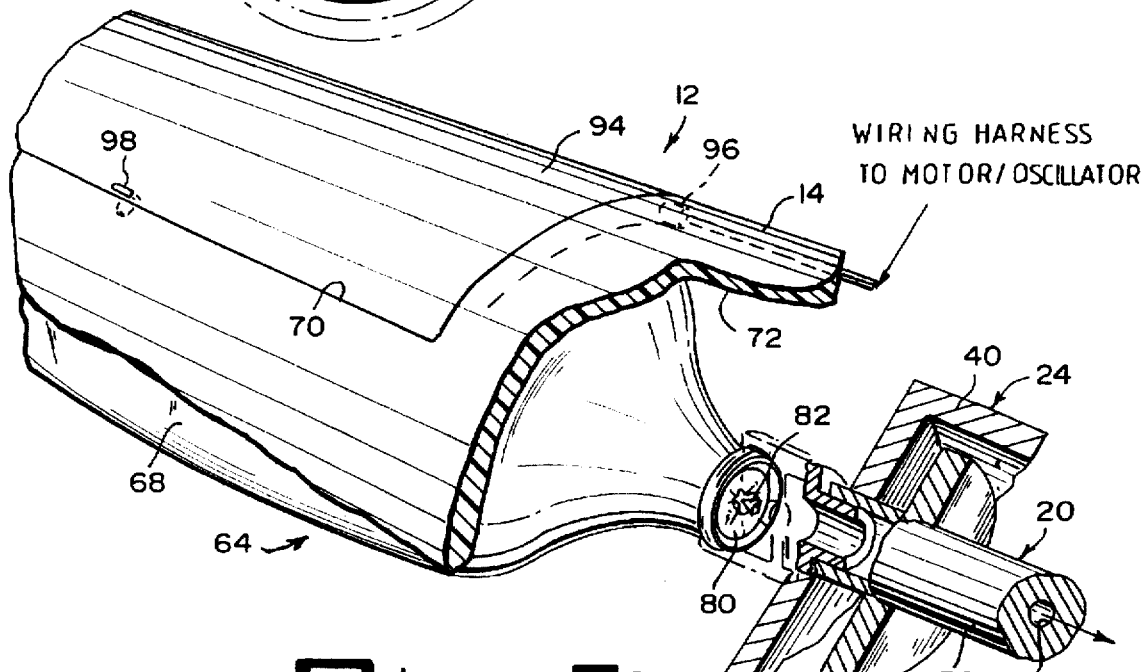

FIG. 7c is a front perspective view with parts broken away and in section taken generally in the direction of arrow 7c in FIG. 7.

Figure 7D:
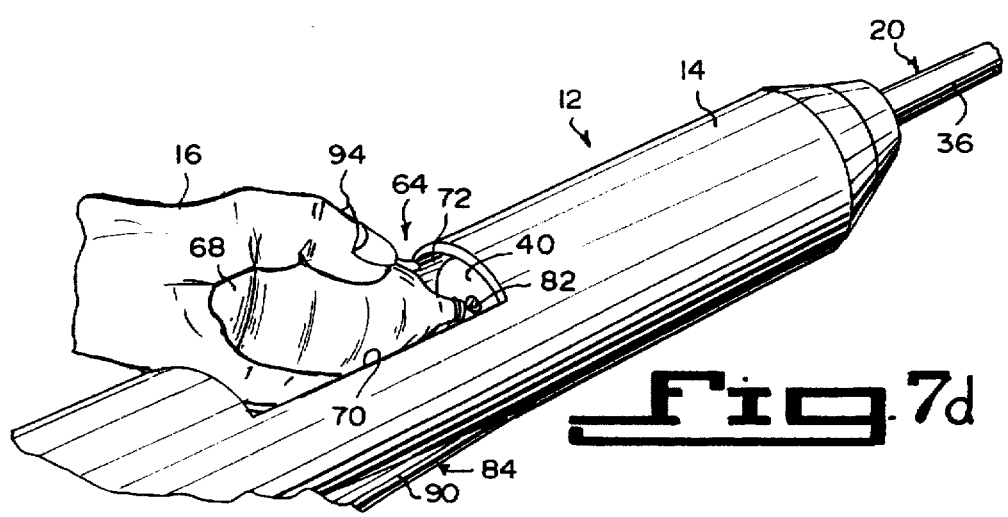

FIG. 7d is a rear perspective view with parts broken away taken generally in the direction of arrow 7d in FIG. 7.

FIG. 8 is an elevational view with parts broken away and in section taken in the direction of arrow 8 in FIG. 5.

FIG. 8a is a rear perspective view taken generally in the direction of arrow 8a in FIG. 8, showing the first embodiment being used by a dentist.

FIG. 9 is a perspective view of a portion of a dentist's office, showing the first embodiment on an instrument tray being recharged by a battery re-charger.

FIG. 10 is a block diagram of the battery charger connected to the first embodiment shown partly in section with parts broken away.

FIG. 11 is a diagrammatic view of the motor and magnetic oscillator mounted on the chuck spindle of the first embodiment.

Similar reference characters denote corresponding features consistently throughout the attached drawings.

DETAILED DESCRIPTION OF THE PREFERRED EMBODIMENTS

Turning now descriptively to the drawings, in which similar reference characters denote similar elements throughout the several views, FIGS. 1 through 11 illustrate a dental hygiene cleaning tool 12 comprising an elongated generally cylindrical housing 14 to be grasped by a hand 16 of a person. A brush bit 18 is provided. A structure 20 is for coupling the brush bit 18 to a first end of the housing 14. A component 22 within the housing 14 is for rotating the brush bit 18. An element 24 within the housing 14 is for rotating the brush bit 18. An element 24 within the housing 14 is for reciprocating the brush bit 18 back and forth, so as to clean plaque build up on teeth and gums 28 of a person 30, to remove bacteria which causes periodontal disease to the gums 28.

The brush bit 18 includes a shank 32 to engage with the coupling structure 20. A brush head 34 is on a distal end of the shank 32 to engage with the teeth 26 and gums 28 of the person 30. The coupling structure 20 is a chuck spindle 36 extending longitudinally from the first end of the elongated housing 14 which will engage with the shank 32 of the brush bit 18.

The rotating component 22 is an electric motor 38 connected centrally to the coupling structure 20, so as to cause the coupling structure 20 to revolve about. The reciprocating element 24 is a magnetic oscillator 40 connected centrally to the coupling structure 20, so as to cause the coupling means 20 to move back and forth.

A power source 42 within the housing 14 is to operate the rotating component 22 and the reciprocating element 24. The power source 42 is a battery 44. A control switch 46 on the housing 14 electrically connects the power source 42 to the rotating component 22 and the reciprocating element 24. When a person grasps the housing 14 by the hand 16, the control switch 46 can be depressed to operate the rotating component 22. When the control switch 46 is moved forward towards the brush bit 18, it will operate the reciprocating element 24.

A removable base 48 is on a second end of the housing 14, so that the battery 44 can be removed and replaced when needed. A facility 50, as shown in FIGS. 5d, 9 and 10 is for recharging the battery 44 within the housing 14 through the base 48.

The recharging facility 50 consists of the base 48 having a built-in socket 52 electrically connected to the battery 44. A recharger stand 54 has a built-in plug 56 which engages with the socket 52 in the base 48. An elongated electric cord 58 is connected at a first end to the recharger stand 54. A transformer with plug 60 is connected to a second end of the elongated electric cord 58 to plug into a wall socket 62, so as to convert 110 VDC to 12 VDC to recharge the battery 44.

As best seen in FIG. 4, the shank 32 of the brush bit 18 can be fabricated straight and curved to help clean the teeth 26 and gums 28. The brush head 34 of the brush bit 18 can be fabricated in various geometric shapes to help clean the teeth 26 and gums 28.

The dental hygiene cleaning tool 12, as best seen in FIGS. 5, 6, 7 through 8, further includes a system 64 within the housing 14, for applying a liquid antiseptic 66 through the brush bit 18, for distribution onto the teeth 26 and gums 28 to help destroy the bacteria which causes periodontal disease to the gums 28.

The applying system 64 contains a compressible cartridge 68 filled with the liquid antiseptic 66. The housing 14 has a side access opening 70 with a longitudinal chamber 72 therein, to receive the compressible cartridge 68. The chuck spindle 36 has a hollow passageway 74 therethrough. The brush bit 18 has a hollow conduit 76 in the shank 32 with release holes 78 at the brush head 34. A puncture membrane 80 is on a forward end of the compressible cartridge 68 (see FIG. 7c). A puncture pin 82 is on a rearward end of the chuck spindle 36 to puncture the puncture membrane 80, so that the liquid antiseptic 66 can be released from the compressible cartridge 68. An assembly 84 in the housing 14 is for forcing the liquid antiseptic 66 out of the compressible cartridge 68, through the hollow passageway 74 in the chuck spindle 36 and past the hollow conduit 76 in the shank 32 and out the release holes 78 at the brush head 34 of the brush bit 18.

The forcing assembly 84 consists of a spring 86 mounted longitudinally within the chamber 72 opposite from the puncture pin 82. A push plate 88 is on a free end of the spring 86. The push plate 88 will bear against the compressible cartridge 68. A compressor lever 90 is hinged at 92 to the housing 14 opposite from the side access opening 70. A portion of the compressor lever 90 extends into the chamber 72. The hand 16 of the person can press the compressor lever 90 to squeeze against the compressible cartridge 68 and force the liquid antiseptic 66 out.

A door 94 is hinged at 96 to the side access opening 70 in the housing 14. A latch member 98 is for keeping the door 92 closed over the side access opening 70 in the housing 14.

LIST OF REFERENCE NUMBERS

| 12 | dental hygiene cleaning tool |
|----|------------------------------|
| 14 | housing of 12 |
| 16 | hand |
| 18 | brush bit of 12 |
| 20 | coupling structure of 12 |
| 22 | rotating component of 12 |
| 24 | reciprocating element of 12 |
| 26 | tooth |
| 28 | gums |
| 30 | person |
| 32 | shank of 18 |
| 34 | brush head of 18 |
| 36 | chuck spindle for 20 |
| 38 | electric motor for 22 |
| 40 | magnetic oscillator for 24 |
| 42 | power source of 12 |
| 44 | battery for 42 |
| 46 | control switch of 12 |
| 48 | removable base of 12 |
| 50 | recharging facility |
| 52 | built-in socket in 48 |
| 54 | recharger stand of 50 |
| 56 | built-in socket in 48 |
| 58 | elongated electric cord of 50 |
| 60 | transformer with plug of 50 |
| 62 | wall socket |
| 64 | applying system |
| 66 | liquid antiseptic |
| 68 | compressible cartridge of 64 |
| 70 | side access opening in 14 |
| 72 | longitudinal chamber in 14 |
| 74 | hollow passageway in 36 |
| 76 | hollow conduit in 32 |
| 78 | release holes in 32 at 34 |
| 80 | puncture membrane on 68 |
| 82 | puncture pin on 36 |
| 84 | forcing assembly of 64 |
| 86 | spring of 84 |
| 88 | push plate of 84 |
| 90 | compressor lever of 84 |
| 92 | hinge for 90 on 14 |
| 94 | door on 14 |
| 96 | hinge for 94 at 70 |
| 98 | latch mechanism for 94 |

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A dental hygiene cleaning tool comprising:
    a) an elongated generally cylindrical housing to be grasped by a hand of a person;
    b) a brush bit having a shank and a brush head;
    c) means for coupling said brush bit to a first end of said housing, said coupling means being a chuck spindle extending longitudinally from said first end of said enlongated housing which will engage with a shank of said brush bit;

d) means within said housing, for rotating said brush bit;

e) means within said housing, for reciprocating said brush bit back and forth, so as to clean plaque build up on teeth and gums of a person, to remove bacteria which causes periodontal disease to the gums; and f) means within said housing for applying a liquid antiseptic through said brush bit, for distribution onto the teeth and gums to help destroy bacteria which causes periodontal disease, said applying means including;

i) a compressible cartridge filled with the liquid antiseptic;

ii) a side access opening in said housing, with a longitudinal chamber therein, to receive said compressible cartridge;

iii) a hollow passageway through said chuck spindle;

iv) a hollow conduit in said shank of said brush bit;

v) release holes in said brush head of said brush bit;

vi) a puncture membrane on a forward end of said compressible cartridge;

vii) a puncture pin on a rearward end of said chuck spindle to puncture said puncture membrane, so that the liquid antiseptic can be released from said compressible cartridge; and viii) means in said housing for forcing the liquid antiseptic out of said compressible cartridge, through said hollow passageway in said chuck spindle and past said hollow conduit in said shank and out said release holes in said brush head of said brush bit.

2. A dental hygiene cleaning tool as recited in claim 1, wherein said brush bit includes:

a) a shank to engage with said coupling means; and b) a brush head on a distal end of said shank to engage with the teeth and gums of the person.

3. A dental hygiene cleaning tool as recited in claim 2, wherein said shank of said brush bit can be fabricated straight and curved to help clean the teeth and gums.

4. A dental hygiene cleaning tool as recited in claim 2, wherein said brush head of said brush bit can be fabricated in various geometric shapes to help clean the teeth and gums.

5. A dental hygiene cleaning tool as recited in claim 2, wherein said coupling means is a chuck spindle extending longitudinally from the first end of said elongated housing which will engage with a shank of said brush bit.

6. A dental hygiene cleaning tool as recited in claim 5, wherein said rotating means is an electric motor connected centrally to said coupling means, so as to cause said coupling means to revolve about.

7. A dental hygiene cleaning tool as recited in claim 6, wherein said reciprocating means is a magnetic oscillator connected centrally to said coupling means, so as to cause said coupling means to move back and forth.

8. A dental hygiene cleaning tool as recited in claim 7, further including a power source within said housing to operate said rotating means and said reciprocating means.

9. A dental hygiene cleaning tool as recited in claim 8, wherein said power source is a battery.

10. A dental hygiene cleaning tool as recited in claim 9, further including a control switch on said housing electrically connecting said power source to said rotating means and said reciprocating means, so that when a person grasps said housing by the hand, said control switch can be depressed to operate said rotating means and when said control switch is moved forward towards said brush bit, it will operate said reciprocating means.

11. A dental hygiene cleaning tool as recited in claim 10, further including a removable base on a second end of said housing, so that said battery can be removed and replaced when needed.

12. A dental hygiene cleaning tool as recited in claim 11, further including means for recharging said battery within said housing through said base.

13. A dental hygiene cleaning tool as recited in claim 12, wherein said recharging means includes:

a) said base having a built-in socket electrically connected to said battery;

b) a recharger stand having a built-in plug which engages with said socket in said base;

c) an elongated electric cord connected at a first end to said recharger stand; and d) a transformer with plug connected to a second end of said elongated electric cord to plug into a wall socket, so as to convert 110 VDC to 12 VDC to recharge said battery.

14. A dental hygiene cleaning tool as recited in claim 13, wherein said shank of said brush bit can be fabricated straight and curved to help clean the teeth and gums.

15. A dental hygiene cleaning tool as recited in claim 14, wherein said brush head of said brush bit can be fabricated in various geometric shapes to help clean the teeth and gums.

16. A dental hygiene cleaning tool as recited in claim 15, further including means within said housing, for applying a liquid antiseptic through said brush bit, for distribution onto the teeth and gums to help destroy the bacteria which causes periodontal disease to the gums.

17. A dental hygiene cleaning tool as recited in claim 16, wherein said forcing means includes:

a) a spring mounted longitudinally within said chamber opposite from said puncture pin;

b) a push plate on a free end of said spring, wherein said push plate will bear against said compressible cartridge; and c) a compressor lever hinged to said housing opposite from said side access opening with a portion of said compressor lever extending into said chamber, so that the hand of the person can press said compressor lever to squeeze against said compressible cartridge and force the liquid antiseptic out.

18. A dental hygiene cleaning tool as recited in claim 17, further including:

a) a door hinged to said side access opening in said housing; and b) a latch member for keeping said door closed over said side access opening in said housing.

19. A dental hygiene cleaning tool as recited in claim 1, wherein said rotating means is an electric motor connected centrally to said coupling means, so as to cause said coupling means to revolve about.

20. A dental hygiene cleaning tool as recited in claim 1, wherein said reciprocating means is a magnetic oscillator connected centrally to said coupling means, so as to cause said coupling means to move back and forth.

21. A dental hygiene cleaning tool as recited in claim 1, further including a power source within said housing to operate said rotating means and said reciprocating means.

22. A dental hygiene cleaning tool as recited in claim 21, wherein said power source is a battery.

23. A dental hygiene cleaning tool as recited in claim 22, further including a removable base on a second end of said housing, so that said battery can be removed and replaced when needed.

24. A dental hygiene cleaning tool as recited in claim 23, further including means for recharging said battery within said housing through said base.

25. A dental hygiene cleaning tool as recited in claim 24, wherein said recharging means includes:
   a) said base having a built-in socket electrically connected to said battery;
   b) a recharger stand having a built-in plug which engages with said socket in said base;
   c) an elongated electric cord connected at a first end to said recharger stand; and
   d) a transformer with plug connected to a second end of said elongated electric cord to plug into a wall socket, so as to convert 110 VDC to 12 VDC to recharge said battery.

26. A dental hygiene cleaning tool as recited in claim 21, further including a control switch on on said housing electrically connecting said power source to said rotating means and said reciprocating means, so that when a person grasps said housing by the hand, said control switch can be depressed to operate said rotating means and when said control switch is moved forward towards said brush bit, it will operate said reciprocating means.

27. A dental hygiene cleaning tool as recited in claim 1, wherein said forcing means includes:
   a) a spring mounted longitudinally within said chamber opposite from said puncture pin;
   b) a push plate on a free end of said spring, wherein said push plate will bear against said compressible cartridge; and
   c) a compressor lever hinged to said housing opposite from said side access opening with a portion of said compressor lever extending into said chamber, so that the hand of the person can press said compressor lever to squeeze against said compressible cartridge and force the liquid antiseptic out.

28. A dental hygiene cleaning tool as recited in claim 1, further including:
   a) a door hinged to said side access opening in said housing; and
   b) a latch member for keeping said door closed over said side access opening in said housing.

\* \* \* \* \*